(12) United States Patent
Han et al.

(10) Patent No.: US 8,658,560 B1
(45) Date of Patent: Feb. 25, 2014

(54) HYDROGENATION CATALYST FOR NITRO-AROMATIC COMPOUNDS AND METHOD FOR PREPARING THE SAME

(71) Applicant: Heesung Catalysts Corporation, Kyeonggi-Do (KR)

(72) Inventors: Hyun Sik Han, Kyeonggi-Do (KR); Young San Yoo, Kyeonggi-Do (KR); Jin Won Kim, Kyeonggi-Do (KR); Kwang Hyun Bak, Jeonlanam-Do (KR)

(73) Assignee: Heesung Catalysts Corporation, Kyeonggi-Do (KR)

( * ) Notice: Subject to any disclaimer, the term of this patent is extended or adjusted under 35 U.S.C. 154(b) by 0 days.

(21) Appl. No.: 13/652,013

(22) Filed: Oct. 15, 2012

(51) Int. Cl.
*B01J 23/60* (2006.01)
*C07C 209/36* (2006.01)

(52) U.S. Cl.
USPC .......................................... 502/329; 564/422

(58) Field of Classification Search
USPC ....................................................... 502/329
See application file for complete search history.

(56) References Cited

U.S. PATENT DOCUMENTS

| | | | | |
|---|---|---|---|---|
| 4,005,177 A | * | 1/1977 | Weidenbach et al. | 423/213.5 |
| 5,258,340 A | * | 11/1993 | Augustine et al. | 502/60 |
| 5,817,896 A | * | 10/1998 | Thomson | 570/176 |
| 7,361,626 B2 | * | 4/2008 | Baijense et al. | 502/329 |
| 7,422,995 B2 | * | 9/2008 | Baijense et al. | 502/329 |
| 7,846,977 B2 | * | 12/2010 | Baijense et al. | 518/700 |
| 2008/0127638 A1 | | 6/2008 | Vaarkamp et al. | |

FOREIGN PATENT DOCUMENTS

| | | |
|---|---|---|
| EP | 0458006 B1 | 11/1991 |
| KR | 1994-6762 | 7/1994 |
| KR | 600546 | 11/2001 |
| KR | 531703 | 11/2005 |
| WO | WO99/28028 A1 | 6/1999 |
| WO | WO00/51728 A1 | 9/2000 |
| WO | WO2007/004774 A1 | 1/2007 |

OTHER PUBLICATIONS

Office Action for U.S. Appl. No. 13/056,284 dated Mar. 14, 2013.

* cited by examiner

*Primary Examiner* — Brian J Davis
(74) *Attorney, Agent, or Firm* — Meunier Carlin & Curfman, LLC

(57) ABSTRACT

The present invention relates to a hydrogenation catalyst for nitro-aromatic compounds, especially nitrobenzene and a method for preparing the same. Particularly, the present invention relates to a hydrogenation catalyst for nitrobenzene, which contains palladium and zinc on a carrier, and is prepared by a process comprising steps of: fixing a zinc component on a carrier; and fixing a palladium component on the carrier on which the zinc component is fixed. Further, it is applicable for a corresponding process for preparing aromatic amino compounds by way of a reaction for hydrogenating nitro-aromatic compounds, and demonstrates improved selectivity, reactivity and stability.

11 Claims, 4 Drawing Sheets

HYDROGENATION CATALYST FOR NITRO-AROMATIC COMPOUNDS AND METHOD FOR PREPARING THE SAME

BACKGROUND

1. Field

The present invention relates to a hydrogenation catalyst for nitro-aromatic compounds and a method for preparing the same, particularly to a hydrogenation catalyst for nitrobenzene. More particularly, the present invention relates to a hydrogenation catalyst for nitrobenzene, which is applicable for a corresponding process for preparing aromatic amino compounds by way of a reaction for hydrogenating aromatic amino compounds and demonstrates improved selectivity, reactivity and stability.

2. Description of the Related Art

Nitro-aromatic compounds, including ortho-toluidine, para-toluidine, toluene diamine prepared by processes for hydrogenating nitrobenzene, nitrotoluene and dinitrotoluene, are widely used as intermediate compounds required in various chemical processes. Especially, aniline is utilized as main raw material to prepare MDI, source material of urethane. A variety of prior arts related to the hydrogenation of nitrobenzene have been already disclosed.

In Korean Patent Notification No. 1994-6772, the method for preparing aniline by hydrogenating nitrobenzene has been mentioned, in which as an applicable catalyst, palladium or palladium-platinum catalysts deposited on a lipophilic carbon are described. In this case, metal oxides or hydroxides such as iron or nickel can be included on a main catalyst carrier. Further, as an accelerator of hydrogenation, zinc compounds can be contained in 20 to 2,000 ppm. In addition, in Korean Patent Registration No. 600546, the hydrogenation catalyst which can be utilized to hydrogenate nitro groups of nitro-aromatic compounds to corresponding amines in the presence of moisture, and the method for preparing the same have been disclosed. The main catalyst applied is described to include nickel such as nickel crystal in a size distribution of bimodal nickel crystal, and have 60 weight % to 80 weight % of nickel content (compared to total weight of catalysts) and 70% or more of recycling rate (after recycling at 100° C. for an hour). Besides, in Korean Patent Registration No. 531703, as a hydrogenation catalyst for nitro-aromatic compounds, Raney nickel catalyst which is prepared by a process comprising steps of: solidifying fused alloy that is comprised of 50 to 90 weight % of aluminum, 10 to 50 weight % of nickel, 0 to 20 weight % of iron, 0 to 15 weight % of cerium, cerium alloy metal, vanadium, niobium, tantalum, chromium, rubidium or manganese, and alternatively, additional glass forming elements, rapidly at a certain cooling speed; and treating the alloy solidified rapidly with organic or inorganic bases, has been disclosed. Furthermore, the hydrogenation catalyst supported in a powder have been disclosed in prior arts, in which active components of the hydrogenation catalyst for nitro-aromatic compounds are comprised of the first precious metal, the second precious metal and a mixture of one or more non-precious metals, wherein the first precious metal is Pt, the second precious metal is Pd, Ru or Rh, and the non-precious metal is V, Fe, Mn, Ce and/or Cr; the first precious metal is Pd, the second precious metal is Ru or Rh, and the non-precious metal is V, Fe, Mn, Ce and/or Cr; or the first precious metal is Pd, the second precious metal is Pt, and the non-precious metal is Ce and/or Cr.

In the process for hydrogenating nitro-aromatic compounds, especially nitrobenzene, a variety of adverse reactions can occur and thus by-products caused by such an adverse action, such as non-aniline compounds becomes severe anti-catalysts against the catalyst used. Moreover, conventional catalysts are found insufficient to acquire desired efficiency in respect of reaction velocity of the hydrogenation. Therefore, it is necessary to improve overall efficiency for preparing aniline, because aniline is widely used for basal raw material of urethane, dyes, medicines and the like. Further, modified catalysts also need to be newly developed.

SUMMARY

The present inventors have attempted to improve selectivity, reactivity and stability of catalysts by modifying conventional catalyst components and as a result, we found that the hydrogenation reaction should increase its efficiency, when palladium and zinc components are fixed on a carrier within a certain concentration range before applying for the hydrogenation of nitrobenzene. Therefore, we have developed a hydrogenation catalyst that can continuously perform the reaction without any procedure discarding non-aniline by-products and completed the present invention successfully. Particularly, the present invention relates to a modified catalyst to prepare aniline continuously by hydrogenating nitrobenzene and a method for manufacturing the same, more particularly to a hydrogenation catalyst for nitrobenzene, wherein palladium-zinc components are deposited and fixed on a carrier sequentially, rather than simultaneously.

DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
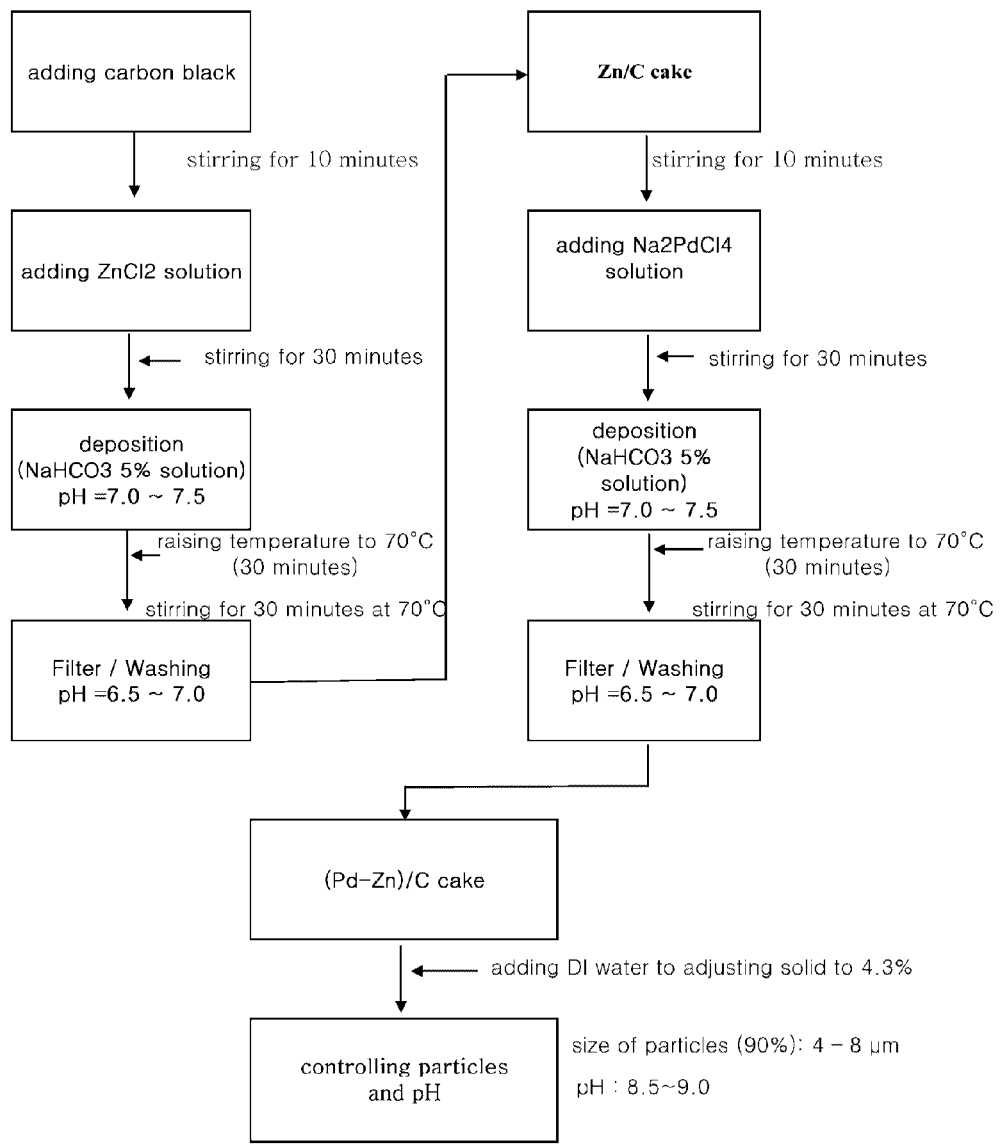
FIG. 1 is a flowchart showing the process for preparing the catalyst according to the present invention.

Hereinafter, the present invention will be described clearly.

The hydrogenation catalyst of the present invention is the palladium-zinc catalyst fixed on a carrier that is selected from a group comprising carbon black, activated carbon, zeolite and alumina, preferably is carbon black. This catalyst can be prepared by a process comprising steps of: fixing a zinc component on carbon black to prepare Zn/C cake preliminarily; and fixing a Pd component additionally on the carrier so as to prepare stable Pd—Zn/C. According to the present invention, the catalyst particles suitable for a process for preparing aniline, have 4 to 20 μm of diameter. The concentration of palladium and zinc deposited and fixed on carbon black is preferably 0.1 to 3 weight % respectively, more preferably 0.5 to 1.5 weight % respectively. The palladium and zinc components are fixed together before use. When one component is just applied, the improvement of reactivity cannot be acquired, but when both components are deposited at the concentration range, the synergic effect, especially the effect associated with activity and selectivity can be acquired for the desired hydrogenation. When the concentrations of palladium and zinc components described in the present invention are over this range, particularly the lowest value or less, the hydrogenation reaction cannot be accomplished efficiently. In contrast, when they are the highest value or more, the main reaction for producing aniline from nitrobenzene is suppressed so as to increase byproducts caused by adverse reactions. When the catalyst of the present invention is used, it is found that other accelerators, including carbonate or bicarbonate salts of alkali metals is not required, even if they are indispensable in former reaction systems to improve the selectivity of hydrogenations. In the meantime, the catalyst prepared according to the present invention can be applied without changing typical conditions of the reaction system. For example, the amount of carbon monoxide mixed with hydrogen is adjusted to 1 to 500 ppm. In the reaction system, a small amount of nitrobenzene is injected through one channel within a reactor, and reacted at 150 to 250° C. under atmospheric pressure to 10 atm. Then, the nitrobenzene added is converted to aniline and water instantly and discarded out of the reaction system in a vapor state.

The present invention provides the method for preparing the hydrogenation catalyst in which zinc and palladium are fixed sequentially on a carbon black carrier. When palladium is solely applied for catalyst component hydrogenating nitrobenzene, the hydrogenation reaction tends to become too strong to control. In this case, it is disadvantageous to result in adverse reactions, decrease life span of catalysts and the like. The present inventors have selected zinc, a transition metal in order to regulate the intensity of hydrogenation and suppress adverse reactions. Aiming at this trial, we have investigated various preparations, and recognized that preparative factors, including sequential fixation of palladium and zinc rather than co-precipitation and pH adjustment, may influence upon reaction velocities and adverse actions. Hereinafter, the process for designing components of the catalyst according to the present invention will be described below. Above all, in order to select components of the catalyst having the synergic effect, palladium is fixed on a carrier, and Co, Mn, Ni, Cu, Fe, Zn and K are deposited. Then, conversion ratios and degrees of adverse reactions generating cyclohexylidene are measured. As a consequence, it is observed that the zinc component should remarkably lower byproducts generated, compared to other components. The present inventors have identified that zinc is an optimal component to regulate the intensity of hydrogenation too high when palladium is solely applied for catalyst component. Further, we have determined that the sequence depositing active components on a carrier may affect the reactivity, because zinc and palladium are different in the adsorptivity from each other. Thus, sequential deposition and fixation is preferable rather than simultaneous deposition. We have also confirmed that when palladium is fixed on a carrier after adsorbing, depositing and fixing zinc on the carrier, the resulting catalyst should increase the catalytic activity highly, compared to that prepared by co-depositing and fixing palladium and zinc. Accordingly, the present invention provides the method for preparing the hydrogenation catalyst for nitro-aromatic compounds, which comprises steps of: fixing a zinc component on a carrier; and fixing a palladium component on the carrier on which the zinc component is fixed. The step the step of fixing a zinc component is comprised of adsorbing a zinc precursor on a carrier; depositing a zinc component with a precipitant; and then, fixing them on the carrier by heating. Preferably, the precipitant is sodium carbonate. An additional step of washing a precipitant is included between the step of fixing a zinc component and the step of fixing a palladium component. The step of fixing a palladium component is comprised of adsorbing a palladium precursor on the carrier on which a zinc component is fixed; depositing a palladium component with a precipitant; and then, fixing them by heating. Preferably, the precipitant is sodium carbonate. Furthermore, an additional step of adjusting pH of final slurry to 8.5 to 9.5 is included, after the step of fixing a palladium component.

Effects

The catalysts according to the present invention can be applied for the processes for hydrogenating nitro-aromatic compounds, especially a reaction system for preparing aniline from nitrobenzene. In order to improve the reactivity, it is suspended in a powder through the reaction system, and reacts rapidly under an anhydrous condition at 150 to 250° C. of temperature. Within the reaction system, aniline and water generated should be removed continuously, and the concentration of non-reacted nitrobenzene should be maintained in 0.01 weight % or less

DESCRIPTION OF THE PREFERRED EMBODIMENTS

Hereinafter, preferred embodiments of the present invention will be described in detail with reference to attached drawings.

EXAMPLES

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation.

Example 1

According to the synthetic procedure illustrated in FIG. 1, Ps—Zn/C catalysts were manufactured in a powder with a 1.7 $m^3$ reactor.

Comparative Example 1

The same procedure was performed as described in Example 1, but the zinc component was substituted by Co, Mn, Ni, Cu, K or Fe components respectively. As a result, comparative catalysts including Pd—Co/C, Pd—Mn/C, Pd—Ni/C, Pd—Cu/C, Pd—K/C and Pd—Fe/C were manufactured.

Experimental Example

Evaluation Test of Catalysts

Figure 2:
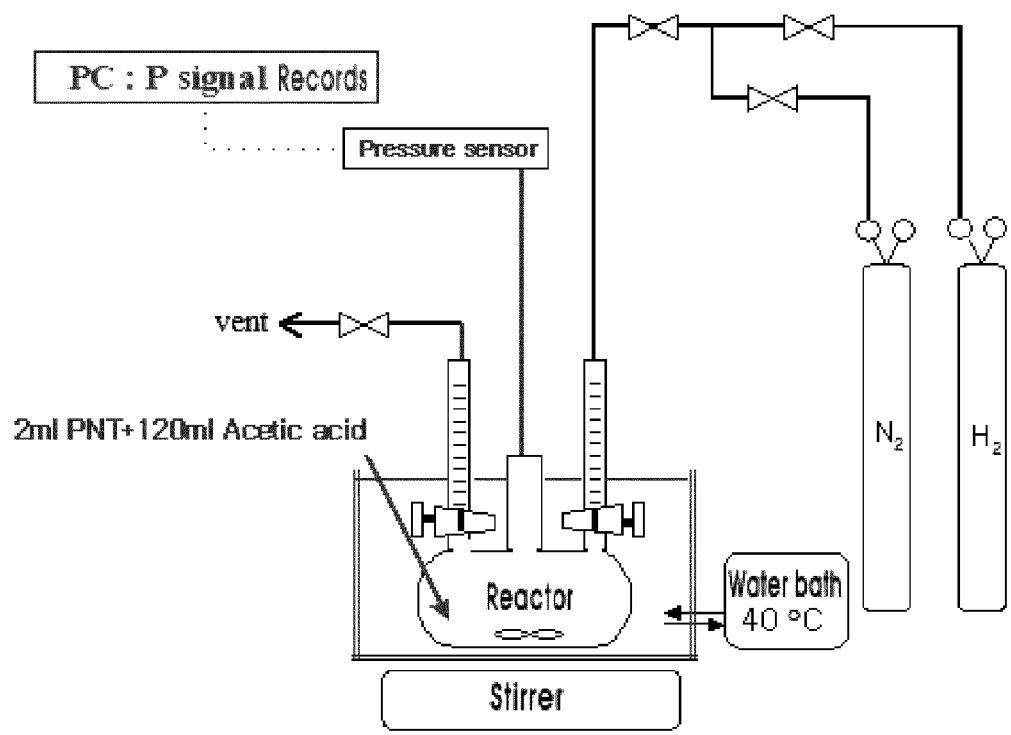
FIG. 2 is a diagram of an apparatus for simple activity tests of catalysts prepared.

In order to evaluate the performance of catalysts manufactured above, the apparatus for simple activity test of catalysts illustrated in FIG. 2 was utilized. The simple activity tests by using this apparatus were conducted with paranitrotoluene (PNT) to evaluate the performance of catalysts manufactured by the process as follows. Above all, the reactor was filled with 0.05 g of catalyst prepared above, PNT and acetic acid reactants and purged twice respectively by using nitrogen-hydrogen gas. Then, the reactor was filled with hydrogen to reach 1.05 $Kgf/cm^2$ or more of inner pressure, closed in both plugs, and started stirring (350 rpm) so as to measure the change of pressure. Then, the time periods changing pressure in 1.0 to 0.9 Kgf/cm² range, were measured to compare catalytic activities.

Figure 3:
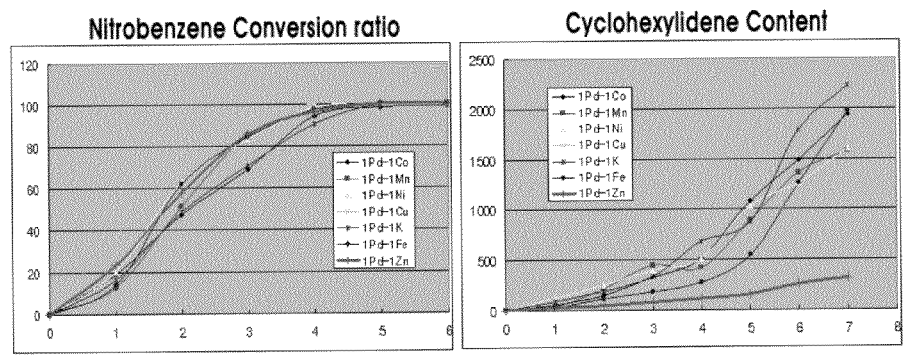
FIG. 3 is comparative graphs showing the activities of transition metals that are fixed respectively on a carrier along with palladium.

FIG. 3 illustrates the conversion ratios of nitrobenzene and the conversion ratios of cyclohexylidene, a byproduct of adverse reaction in between the catalyst of this invention prepared in Example 1 and the catalysts prepared in Comparative Example. As a result, it is observed that when fixing with Pd on a carrier, the zinc component should suppress adverse reactions outstandingly compared to Co, Mn, Ni, Cu, K or Fe components.

On the other hand, the simple activity of the catalyst prepared in Example 1 by the process illustrated in FIG. 1 was measured to 155 unit, the simple activity of the catalyst prepared by the process that co-precipitates a zinc precursor and a palladium precursor to fix on a carrier was measured to 100 unit, and the simple activity of the catalyst prepared by the process that deposits a zinc component with sodium carbonate primarily, and adsorbs a palladium precursor sequentially to fix was measured to 130 unit. Therefore, the catalyst prepared by the method according to the present invention, especially the process that fixes a zinc component primarily by heating, and fixes a palladium component secondarily, is outstanding in the activity. Similar experiments were repeated a lot. As a consequence, it is found that the activities of catalysts become better when it is prepared by washing out a precipitant after fixing a zinc component primarily. Further, the activity and the stability of catalysts are improved when the catalysts prepared are stored at a slightly alkali pH.

Comparative Example 2

Figure 4:
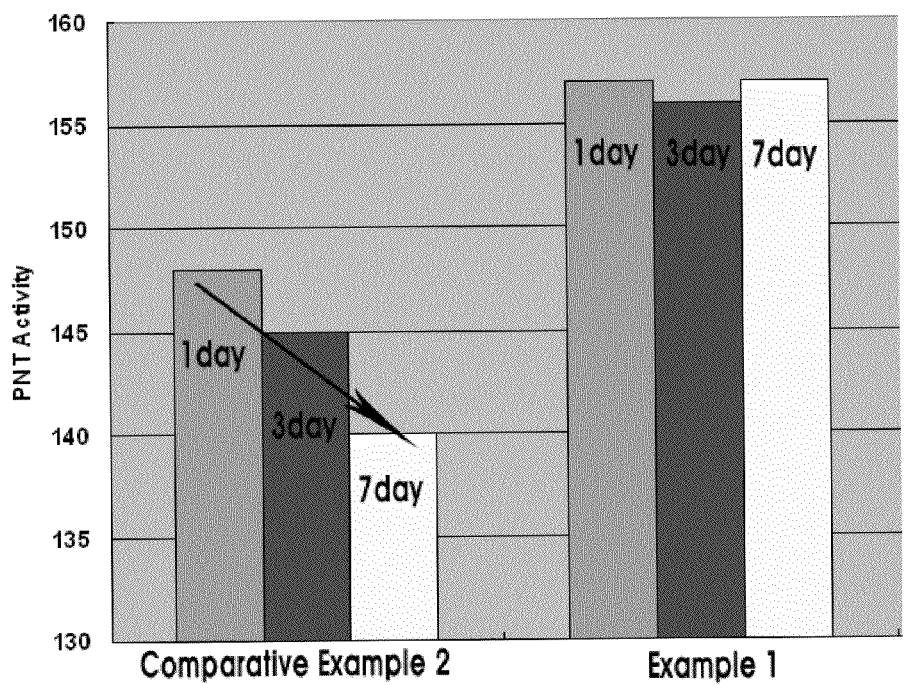
FIG. 4 is a comparative graph showing the stabilities of catalysts.

The same procedure was performed as described in Example 1, but pH was adjusted to 7.0 at a final stage to prepare Pd—Zn/C catalysts in a slurry type. As illustrated in FIG. 4, it is observed that the catalyst prepared in Example 1 has a higher catalytic activity and maintains the activity outstandingly, compared to that of Comparative Example 2.

Figure 5:
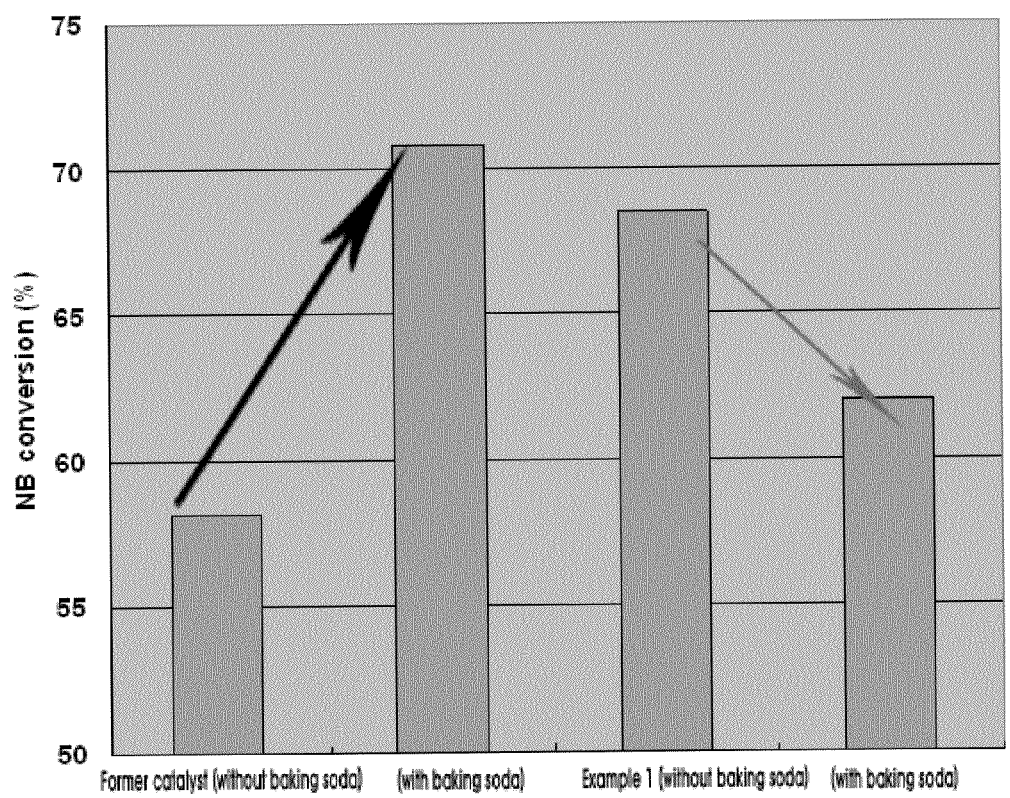
FIG. 5 is a comparative graph showing the effect of baking soda added to a system for hydrogenating nitrobenzene.

In prior arts, former reaction systems for hydrogenating nitrobenzene have required to apply baking soda. That is to say, typical catalysts for hydrogenating nitrobenzene improved the reaction activity of hydrogenation by adding baking soda. It is found that the hydrogenation catalyst for nitrobenzene according to the present invention is seldom affected by such a baking soda. Rather, the baking soda lowers the reactivity when added the reaction system. FIG. 5 illustrates that the reactivity of a conventional catalytic system becomes higher by adding baking soda, but the reactivity of the catalyst prepared in Example 1 becomes lower by adding baking soda. Therefore, the catalytic system according to the present invention is advantageous to simplify the procedure of reactions, increase the purity of products and the like, without ancillary catalytic factor increasing the reactivity such as baking soda etc.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A hydrogenation catalyst for nitro-aromatic compounds, which contains palladium and zinc on a carrier, and is prepared by a process comprising steps of: fixing a zinc component on a carrier; fixing a palladium component on the carrier on which the zinc component is fixed to thereby provide a catalyst slurry; and then adjusting pH of the catalyst slurry to 8.5 to 9.5.

2. The hydrogenation catalyst for nitro-aromatic compounds according to claim 1, wherein the step of fixing a zinc component is comprised of adsorbing a zinc precursor on a carrier; depositing a zinc component with a precipitant; and then, fixing by heating.

3. The hydrogenation catalyst for nitro-aromatic compounds according to claim 2, wherein the precipitant is sodium carbonate.

4. The hydrogenation catalyst for nitro-aromatic compounds according to claim 2, wherein an additional step of washing the precipitant is included between the step of fixing a zinc component and the step of fixing a palladium component.

5. The hydrogenation catalyst for nitro-aromatic compounds according to claim 1, wherein the step of fixing a palladium component is comprised of adsorbing a palladium precursor on the carrier on which a zinc component is fixed; depositing a palladium component with a precipitant; and then, fixing by heating.

6. The hydrogenation catalyst for nitro-aromatic compounds according to claim 1, wherein the carrier is selected from the group consisting of carbon black, activated carbon, zeolite and alumina.

7. The hydrogenation catalyst for nitro-aromatic compounds according to claim 1, wherein the catalyst particles are 4 to 20 μm in diameter.

8. The hydrogenation catalyst for nitro-aromatic compounds according to claim 1, wherein the palladium is present at 0.1 to 3 weight % and the zinc is present at 0.1 to 3 weight %.

9. A method for preparing a hydrogenation catalyst for nitro-aromatic compounds, comprising the steps of fixing a zinc component on a carrier; fixing a palladium component on the carrier on which the zinc component is fixed to thereby provide a catalyst slurry; and then adjusting pH of the catalyst slurry to 8.5 to 9.5.

10. A method for preparing an aromatic amino compound, which comprises a step of hydrogenating nitro-aromatic compounds, wherein the hydrogenation is performed in the presence of the catalyst defined in claim 1.

11. The method for preparing an aromatic amino compound according to claim 10, wherein the aromatic amino compound contains aniline compounds.

* * * * *